United States Patent [19]
Holland et al.

[11] Patent Number: 6,060,649
[45] Date of Patent: May 9, 2000

[54] INBRED CORN LINE AS607

[75] Inventors: Gregory J. Holland, Cedar Falls; Gregory G. Wandrey, Ankeny, both of Iowa

[73] Assignee: Asgrow Seed Company, Kalamazoo, Mich.

[21] Appl. No.: 08/925,775

[22] Filed: Sep. 9, 1997

[51] Int. Cl.[7] .............................. A01H 5/00; A01H 4/00; A01H 1/00; C12N 5/04
[52] U.S. Cl. ........................ 800/320.1; 800/298; 800/275; 800/271; 435/412; 435/424; 435/430; 435/430.1
[58] Field of Search .................................. 800/320.1, 298, 800/275, 271, 303, 274; 435/412, 424, 430, 430.1

[56] References Cited

PUBLICATIONS

Phillips et al. "Cell/tissue Culture and in vitro manipulation" Corn & Corn Improvement, ed SPrague et al. pp. 358, 1988.

*Primary Examiner*—Gary Benzion
*Attorney, Agent, or Firm*—Rothwell, Figg, Ernst & Kurz

[57] ABSTRACT

An inbred corn line, designated 3114, is disclosed. The invention relates to the seeds of inbred corn line 3114, to the plants of inbred corn line 3114 and to methods for producing a corn plant produced by crossing the inbred line 3114 with itself or another corn line. The invention further relates to hybrid corn seeds and plants produced by crossing the inbred line 3114 with another corn line.

13 Claims, No Drawings

INBRED CORN LINE AS607

BACKGROUND OF THE INVENTION

The present invention relates to a new and distinctive corn inbred line, designated ASG07. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior corn inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new corn inbred line.

The development of commercial corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop stable, high yielding corn hybrids that are agronomically sound. The reasons for this goal are obviously to maximize the amount of grain produced on the land used and to supply food for both animals and humans. To accomplish this goal, the corn breeder must select and develop corn plants that have the traits that result in superior parental lines for producing hybrids.

SUMMARY OF THE INVENTION

According to the invention, there is provided a novel inbred corn line, designated ASG07. This invention thus relates to the seeds of inbred corn line ASG07, to the plants of inbred corn line ASG07 and to methods for producing a corn plant produced by crossing the inbred line ASG07 with itself or another corn line. This invention further relates to hybrid corn seeds and plants produced by crossing the inbred line ASG07 with another corn line.

DETAILED DESCRIPTION OF THE INVENTION

In the description and tables which follow, a number of terms are used. In order to provide a clear and consistent understanding of the specification and claims, including the scope to be given such terms, the following definitions are provided:

Yield (Bushels/Acre). The yield in bushels/acre is the actual yield of the grain at harvest adjusted to 15.5% moisture.

Moisture. The moisture is the actual percentage moisture of the grain at harvest.

Stalk Lodging (STALK). This is a relative rating for stalk lodging, where a lower score or number indicates a lower amount of stalk lodging while a higher number indicates a higher level of stalk lodging is present.

Root Lodging (ROOT). This is a relative rating for root lodging, i.e., those plants that lean from a vertical axis at an approximate 30° angle or greater would be counted as root lodged. Root lodging is scored ranging from 1 to 9, with a score of "1" meaning excellent roots with low to zero root lodging, while the high score of 9 indicates a very high level of root lodging is present.

Stay Green (S.GR). Stay Green is a rating ranging from 1 to 9. A genotype having a rating of "1" has relatively dry and loose open husks combined with the remainder of the plant being relatively green and free of diseases. A high rating of "9" indicates a genotype having relatively green and wet husks on a plant with diseased and/or drying leaf tissue.

Plant Height. This is a measure of the height of the hybrid from the ground to the tip of the tassel, and is measured in centimeters.

Field Score (F.SC). This is a measure of the intactness of the plant at harvest time and is rated from 1 to 9. A rating of "1" means a relatively fully intact plant, where the plant has its tassel and leaves still on the plant. The highest score of 9 means a plant where the tassel and/or top portion of the plant and many of the leaves have been dislodged and broken off of the plant.

Ear Height (E.HT). The ear height is a measure from the ground to the ear node attachment, and is measured in centimeters.

Test Weight (T.WT). Test weight is the grain density measured in pounds per bushel.

Inbred corn line ASG07 is a yellow dent corn with superior characteristics, and provides an excellent parental line in crosses for producing first generation ($F_1$) hybrid corn.

ASG07 is a corn inbred line developed from the cross of LH82×ASG08 which was then selfed and the pedigree system of plant breeding was then used to develop ASG07. Yield, stalk quality, root quality, disease tolerance, late plant greenness, late plant intactness, ear retention, pollen shedding ability, silking ability and corn borer tolerance were the criteria used to determine the rows from which ears were selected.

Inbred corn line ASG07 has the following morphologic and other characteristics (based primarily on data collected at Kalamazoo, Michigan).

VARIETY DESCRIPTION INFORMATION

1. TYPE: Dent
2. REGION WHERE DEVELOPED: Northcentral U.S.
3. MATURITY:

|  | Days | Units |
| --- | --- | --- |
| From emergence to 50% of plants in silk: | 70 | 1427 |
| From emergence to 50% of plants in pollen | 72 | 1464 |
| From 10% to 90% pollen shed | 4 |  |

4. PLANT:
   Plant Height (to tassel tip): 177.3 cm
   Ear Height (to base of top ear): 78.8 cm
   Average Length of Top Ear Internode: 13.2 cm
   Average number of Tillers: 0
   Average Number of Ears per Stalk: 1.8
   Anthocyanin of Brace Roots: Moderate
5. LEAF:
   Width of Ear Node Leaf: 8.9 cm
   Length of Ear Node Leaf: 61.7 cm
   Number of leaves above top ear: 5
   Leaf Angle from 2nd Leaf above ear at anthesis to Stalk above leaf: 29°
   Leaf Color: Munsell Code 5 GY 4/4
   Leaf Sheath Pubescence (Rate on scale from 1=none to 9=like peach fuzz): 2
   Marginal Waves (Rate on scale from 1=none to 9=many): 4
   Longitudinal Creases (Rate on scale from 1=none to 9=many): 3
6. TASSEL:
   Number of Lateral Branches: 7
   Branch Angle from Central Spike: 8
   Tassel Length (from top leaf collar to tassel top): 33.3 cm
   Pollen Shed (Rate on scale from 0=32 male sterile to 9=heavy shed): 5
   Anther Color: Munsell Code 5Y 8/6
   Bar Glumes: Absent
7a. EAR: (Unhusked Data)
   Silk Color (3 days after emergency): Munsell Code 2.5GY 8/6
   Fresh Husk Color (25 days after 50% silking): Munsell Code 2.5GY 8/8
   Dry Husk Color (65 days after 50% silking): Munsell Code 5Y 8/4
   Position of Ear: Pendent
   Husk Tightness (Rate on scale from 1= very loose to 9= very tight): 2
   Husk Extension: Medium (<8 cm)
7b. EAR: (Husked Ear Data)
   Ear Length: 11.8 cm
   Ear Diameter at mid-point: 3.1 mm
   Ear Weight: 62.8 gm
   Number of Kernel Rows: 14
   Kernel Rows: Distinct
   Row Alignment: Slightly curved
   Shank Length: 9.4 cm
   Ear Taper: Average
8. KERNAL: (Dried)
   Kernel Length: 9.4 mm
   Kernel Width: 6.4 mm
   Kernel Thickness: 2.6 mm
   Aleurone Color Pattern: Homozygous
   Aleurone Color: Munsell code 2.5Y 8/8
   Hard Endosperm Color—Munsell code 2.5 Y 8/8
   Endosperm Type: Normal Starch
9. COB:
   Cob Diameter at mid-point: 17.4 mm
   Cob Color: Munsell code 10 R 7/6

This invention is also directed to methods for producing a corn plant by crossing a first parent corn plant with a second parent corn plant, wherein the first or second corn plant is the inbred corn plant from the line ASG07. Further, both first and second parent corn plants may be from the inbred line ASG07. Therefore, any methods using the inbred corn line ASG07 are part of this invention: selfing, backcrosses, hybrid breeding, and crosses to populations. Any plants produced using inbred corn line ASG07 as a parent are within the scope of this invention. Advantageously, the inbred corn line is used in crosses with other corn varieties to produce first generation ($F_1$) corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or parts of plants, such as pollen, flowers, kernels, ears, cobs, leaves, husks, stalks, and the like.

Tissue culture of corn is described in European Patent Application, Publication No. 160,390, incorporated herein by reference. Corn tissue culture procedures are also described in Green and Rhodes, "Plant Regeneration in Tissue Culture of Maize", *Maize for Biological Research* (Plant Molecular Biology Association, Charlottesville, Va. 1982), at 367–372. Thus, another aspect of this invention is to provide for cells which upon growth and differentiation produce the inbred line ASG07.

LH82 and ASG08 are the progenitors of ASG07. LH82 is a proprietary field corn inbred line of Holden's Foundation Seeds, Inc. of Williamsburg, Iowa and ASG08 is a proprietary field corn inbred line of Asgrow Seed Company of Kalamazoo, Michigan.

ASG07 is most similar to LH82, however there are numerous differences including: The ear of ASG07 is approximately 33% lighter in weight than LH82. ASG07 averages 15 rows of kernel per ear as compared to LH82 averaging 21.5 rows.

Some of the criteria used to select ears in various generations include: yield, stalk quality, root quality, disease tolerance, late plant greenness, late season plant intactness, ear retention, pollen shedding ability, silking ability, and corn borer tolerance. During the development of the line, crosses were made to inbred testers for the purpose of estimating the line's general and specific combining ability, and evaluations were run by the Schoolcraft, Michigan Breeding Station. The inbred was evaluated further as a line and in numerous crosses by Schoolcraft and other breeding stations across the Corn Belt. The inbred has proven to have a very good combining ability in hybrid combinations.

The inbred has shown uniformity and stability for all traits. It has been self-pollinated and ear-rowed a sufficient number of generations, with careful attention to uniformity of plant type to ensure homozygosity and phenotypic stability. The line has been increased both by hand and sibbed in isolated fields with continued observations for uniformity. No variant traits have been observed or are expected in ASG07.

TABLES

In the tables that follow, the traits and characteristics of inbred corn line ASG07 are given in hybrid combination. The data collected on inbred corn line ASG07 is presented for the key characteristics and traits. The tables present yield test information about ASG07. ASG07 was tested in several hybrid combinations at numerous locations, with two or three replications per location. Information about these hybrids, as compared to several check hybrids, is presented.

The first pedigree listed in the comparison group is the hybrid containing ASG07. Information for the pedigree includes:

In column 1, the first genotype listed (in row 1) is the hybrid containing ASG07 and the second genotype listed in row 2 is another hybrid. Statistical information including the LSD, probability, number of tests and number of years are shown in rows 3 through 6 of each table. Columns 2, 3 and 4 show the bushels/acre, moisture and yield to moisture ratio for each genotype. In columns 5, 6 and 7 information for the genotype includes: stalk lodging (STALK), root lodging (ROOT) and stay green scores (S.GR). Columns 8, 9 and 10 indicate the fall scores (F.SC), ear height (E.HT) and test weight (T.WT).

The series of hybrids listed under the hybrid containing ASG07 are considered check hybrids. These check hybrids are compared to hybrids containing the inbred ASG07.

TABLE 1

|  | BU/A | MOIST | Y:MO | STALK | ROOTS | S.GR | F.SC | E.HT | T.WT |
|---|---|---|---|---|---|---|---|---|---|
| Asgrow SS/ASG07 | 159.6 | 20.50 | 147.1 | 3.151 | 1.923 | 4.036 | 4.310 | 110.1 | 55.30 |
| Pioneer 3751 | 150.6 | 18.29 | 143.2 | 8.239 | 1.885 | 5.536 | 5.506 | 104.4 | 55.76 |
| LSD .05 (95% confidence) | 3.708 | .280 | 3.803 | 1.401 | .456 | .454 | .328 | 4.028 | .534 |
| Probability of equal means | .000 | .000 | .042 | .000 | .867 | .000 | .000 | .007 | .085 |
| Number of tests compared | 93 | 93 | 93 | 101 | 39 | 28 | 84 | 42 | 92 |
| Number of years | 2 | 2 | 2 | 2 | 2 | 2 | 2 | 2 | 2 |

TABLE 2

|  | BU/A | MOIST | Y:MO | STALK | ROOTS | S.GR | F.SC | E.HT | T.WT |
|---|---|---|---|---|---|---|---|---|---|
| Asgrow SS/ASG07 | 162.1 | 20.71 | 149.0 | 3.197 | 2.176 | 3.500 | 4.348 | 110.7 | 54.41 |
| Pioneer 3753 | 158.6 | 18.32 | 151.1 | 9.568 | 2.324 | 6.500 | 5.409 | 105.6 | 56.91 |
| LSD .05 (95% confidence) | 5.406 | .466 | 5.555 | 3.171 | 1.471 | 1.149 | .509 | 6.055 | .478 |
| Probability of equal means | .198 | .000 | .469 | .000 | .835 | .001 | .000 | .098 | .000 |
| Number of tests compared | 40 | 40 | 40 | 43 | 17 | 6 | 33 | 22 | 40 |
| Number of years | 1 | 1 | 1 | 1 | 1 | 1 | 1 | 1 | 1 |

TABLE 3

|  | BU/A | MOIST | Y:MO | STALK | ROOTS | S.GR | F.SC | E.HT | T.WT |
|---|---|---|---|---|---|---|---|---|---|
| Asgrow SS/ASG07 | 167.4 | 19.81 | 156.5 | 2.922 | 1.857 | 4.931 | 4.428 | 104.3 | 55.95 |
| Pioneer 3563 | 164.5 | 20.40 | 152.0 | 4.760 | 1.617 | 3.862 | 4.047 | 104.5 | 57.40 |
| LSD .05 (95% confidence) | 2.594 | .294 | 2.597 | .663 | .356 | .299 | .182 | 2.706 | .466 |
| Probability of equal means | .027 | .000 | .001 | .000 | .181 | .000 | .000 | .873 | .000 |
| Number of tests compared | 251 | 251 | 251 | 228 | 98 | 87 | 2222 | 97 | 248 |
| Number of years | 3 | 3 | 3 | 3 | 3 | 3 | 3 | 3 | 3 |

TABLE 4

|  | BU/A | MOIST | Y:MO | STALK | ROOTS | S.GR | F.SC | E.HT | T.WT |
|---|---|---|---|---|---|---|---|---|---|
| Asgrow SS/ASG07 | 166.0 | 19.74 | 154.8 | 2.961 | 1.773 | 4.969 | 4.440 | 104.2 | 55.79 |
| Dekalb DK512 | 165.9 | 19.15 | 155.8 | 6.489 | 1.282 | 5.531 | 5.339 | 104.8 | 54.02 |
| LSD .05 (95% confidence) | 2.362 | .197 | 2.408 | 1.168 | .300 | .231 | .171 | 2.443 | .187 |
| Probability of equal means | .951 | .000 | .386 | .000 | .001 | .000 | .000 | .647 | .000 |
| Number of tests compared | 316 | 316 | 317 | 277 | 110 | 96 | 277 | 106 | 310 |
| Number of years | 3 | 3 | 3 | 3 | 3 | 3 | 3 | 3 | 3 |

TABLE 5

|  | BU/A | MOIST | Y:MO | STALK | ROOTS | S.GR | F.SC | E.HT | T.WT |
|---|---|---|---|---|---|---|---|---|---|
| Common Asgrow SS/ASG07 | 165.7 | 19.54 | 155.5 | 4.501 | 3.000 | 3.667 | 4.571 | 113.5 | 55.43 |
| Common Asgrow SS/LH179 | 144.3 | 20.29 | 132.4 | 8.334 | 1.167 | 4.667 | 4.714 | 100.3 | 54.92 |
| LSD .05 (95% confidence) | 7.934 | .893 | 8.249 | 4.351 | 2.924 | 4.300 | 1.083 | 8.621 | .825 |
| Probability of equal means | .000 | .093 | .000 | .080 | .168 | .423 | .780 | .007 | .203 |
| Number of tests compared | 14 | 14 | 14 | 18 | 6 | 3 | 14 | 10 | 14 |
| Number of years | 1 | 1 | 1 | 1 | 1 | 1 | 1 | 1 | 1 |

TABLE 6

|  | BU/A | MOIST | Y:MO | STALK | ROOTS | S.GR | F.SC | E.HT | T.WT |
|---|---|---|---|---|---|---|---|---|---|
| Common Asgrow SS/ASG07 | 166.9 | 19.68 | 156.1 | 1.537 | 2.400 | 5.125 | 4.368 | 100.7 | 55.60 |
| Common Asgrow SS/LH168 | 161.2 | 21.00 | 147.3 | 4.045 | 1.400 | 4.000 | 4.395 | 102.5 | 56.69 |
| LSD .05 (95% confidence) | 6.482 | .549 | 6.442 | 1.301 | 2.780 | .537 | .711 | 6.615 | .671 |
| Probability of equal means | .085 | .000 | .010 | .001 | .374 | .002 | .939 | .571 | .003 |
| Number of tests compared | 19 | 19 | 19 | 17 | 5 | 8 | 19 | 13 | 19 |
| Number of years | 1 | 1 | 1 | 1 | 1 | 1 | 1 | 1 | 1 |

DEPOSIT INFORMATION

A deposit of the Asgrow Seed Company proprietary inbred corn line ASG07 disclosed above and recited in the appended claims has been made with the American Type Culture Collection (ATCC), 10801 University Boulevard, Manassas, Va. 20110. The date of deposit was Apr. 14, 1999. The deposit of 2,500 seeds were talon from the same deposit maintained by Asgrow Seed Company since prior to the filing date of this application. All restrictions upon the deposit have been removed, and the deposit is intended to meet all of the requirements of 37 C.F.R. §1.801–1.809. The ATCC accession number is ATCC 203933. The deposit will be maintained in the depository for a period of 30 years, or 5 years after the last request, or for the effective life of the patent, whichever is longer, and will be replaced as necessary dung that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred corn seed designated ASG07 having ATCC accession No. 203933.

2. A plant or its parts produced by growing the seed of claim 1.

3. Pollen of the plant of claim 2.

4. An ovule of the plant of claim 2.

5. A corn plant having all of the physiological and morphological characteristics of the plant of claim 2.

6. Tissue culture of the plant of claim 2.

7. A corn plant regenerated from the tissue culture of claim 6, wherein said corn plant is capable of expressing all the physiological and morphological characteristics of inbred corn line 3114.

8. A method for producing a hybrid corn seed comprising crossing a first inbred parent corn plant with a second inbred parent corn plant and harvesting the resultant hybrid corn seed, wherein said first or second parent corn plant is the corn plant of claim 2.

9. A hybrid seed produced by the method of claim 8.

10. A hybrid plant or its parts produced by growing said hybrid corn seed of claim 9.

11. A method for producing a hybrid corn seed comprising crossing an inbred plant according to claim 2 with another, different corn plant and harvesting the resultant seed.

12. A hybrid seed produced by the method of claim 11.

13. A hybrid plant or its parts produced by growing said hybrid corn seed of claim 12.

* * * * *